(12) United States Patent
Murata et al.

(10) Patent No.: US 8,278,361 B2
(45) Date of Patent: Oct. 2, 2012

(54) FLUOROALKYL ALCOHOL MIXTURE AND METHOD FOR PRODUCING THE SAME

(75) Inventors: Seiichiro Murata, Ibaraki (JP); Masayosi Horiuti, Ibaraki (JP); Katsuyuki Sato, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 187 days.

(21) Appl. No.: 12/863,464

(22) PCT Filed: Jan. 20, 2009

(86) PCT No.: PCT/JP2009/050744
§ 371 (c)(1),
(2), (4) Date: Jul. 19, 2010

(87) PCT Pub. No.: WO2009/093567
PCT Pub. Date: Jul. 30, 2009

(65) Prior Publication Data
US 2010/0288971 A1 Nov. 18, 2010

(30) Foreign Application Priority Data
Jan. 24, 2008 (JP) ................................ 2008-013385

(51) Int. Cl.
B01F 17/38 (2006.01)
C07C 33/42 (2006.01)
C07C 29/09 (2006.01)
C09K 3/00 (2006.01)
C11D 1/825 (2006.01)

(52) U.S. Cl. .................... 516/204; 568/843; 568/847

(58) Field of Classification Search ............... 568/842, 568/841, 843, 847, 849, 891; 516/204
See application file for complete search history.

(56) References Cited

U.S. PATENT DOCUMENTS

| | | | | |
|---|---|---|---|---|
| 3,171,861 A | * | 3/1965 | Ahlbrecht | 568/842 |
| 3,285,975 A | * | 11/1966 | Ahlbrecht | 568/843 |
| 3,324,187 A | * | 6/1967 | Litt et al. | 568/811 |
| 3,576,888 A | * | 4/1971 | Lichstein et al. | 568/843 |
| 3,810,939 A | * | 5/1974 | Ray-Chaudhuri et al. | 562/113 |
| 4,754,082 A | * | 6/1988 | Raab et al. | 568/843 |
| 5,268,122 A | * | 12/1993 | Rao et al. | 510/411 |

FOREIGN PATENT DOCUMENTS

| | | |
|---|---|---|
| JP | 44-1216 B1 | 1/1969 |
| JP | 46-5447 B1 | 2/1971 |
| JP | 59-108081 | 6/1984 |
| JP | 63-22530 A | 1/1988 |
| JP | 2000-038361 A | 2/2000 |

OTHER PUBLICATIONS

Derwent Abstract, week 201110, London: Derwent Publications Ltd., AN 2009-M03823, JP 2009173576 A,& US 20100288971 A1 (UNIMATEC Co Ltd), abstract, pp. 1-5.*
Machine Translation of Publ. No. JP 2009-173576-071509, published Jun. 2009, Japan patent Office, Tokyo, Japan, obtained online @ http://dossier1.ipdl.inpit.go.jp/AIPN/odse_top_dn.ipdl?N0000= 7400 (Downloaded Mar. 25, 2012), pp. 1-13.*
Dmowski, W. et al., "Fluorination of Some Fluorine-Containing Oxo Esters by Sulfur Tetrafluoride", *Journal of Fluorine Chemistry*, 1995, 74(2), pp. 259-260.
Feiring, Andrew E. et al., Reaction of Perfluoroalkylethylens With Nucleophiles, *Journal of Fluorine Chemistry*, 1984, 24(1), pp. 125-132.
International Search Report from corresponding PCT/JP2009/050744, dated Apr. 14, 2009, 4 pages.
International Preliminary Report on Patentability and Written Opinion of the International Search Report from corresponding PCT application No. PCT/JP2009/050744 dated Sep. 10, 2010, 5 pgs.

* cited by examiner

*Primary Examiner* — Daniel S Metzmaier
(74) *Attorney, Agent, or Firm* — Brinks Hofer Gilson & Lione

(57) ABSTRACT

Disclosed is a mixture of fluoroalkyl alcohols represented by the general formulae: $CF_3(CF_2)_n(CH=CF)_a(CF_2CF_2)_b(CH_2CH_2)_cOH$ [Ia] and $CF_3(CF_2)_{n-1}(CF=CH)_aCF_2(CF_2CF_2)_b(CH_2CH_2)_cOH$ [Ib], wherein n is an integer of 1 to 5, a is an integer of 1 to 4, b is an integer of 0 to 3, and c is an integer of 1 to 3. This fluoroalkyl alcohol mixture is produced by the reaction of a fluoroalkyl iodide represented by the general formula: $CF_3(CF_2)_n(CH_2CF_2)_a(CF_2CF_2)_b(CH_2CH_2)_c$ I [II], with N-methylformamide, followed by hydrolysis in the presence of a basic compound.

2 Claims, No Drawings

FLUOROALKYL ALCOHOL MIXTURE AND METHOD FOR PRODUCING THE SAME

RELATED APPLICATION

This application is a 35 U.S.C. §371 national phase filing of International Patent Application No. PCT/JP2009/050744, filed Jan. 20, 2009, through which and to which priority is claimed under 35 U.S.C. §119 to Japanese Patent Application No. 2008-013385, filed Jan. 24, 2008.

TECHNICAL FIELD

The present invention relates to a mixture of fluoroalkyl alcohols and a method for producing the same. More specifically, the present invention relates to a mixture of fluoroalkyl alcohols that are effectively used as surfactants, etc., and a method for producing the same.

BACKGROUND ART

Acrylic acid derivatives of perfluoroalkyl alcohols (e.g., $CF_3(CF_2)_7CH_2CH_2OCOCH=CH_2$) are used in large amounts as monomers for synthesizing water- and oil-repellent for textile. Moreover, perfluoroalkyl alcohols serving as starting material of the acrylic acid derivative are widely used as surfactants, etc.

[Patent Document 1] JP-B-63-22237

However, it has been recently reported that perfluorooctanoic acid having eight carbon atoms or perfluorocarboxylic acids having more than eight carbon atoms have adverse effect on the environment, because they are hardly degradability and having high bioaccumulation potential, and may exhibit toxicity to organisms. Among these compounds, those containing a perfluoroalkyl group having eight or more carbon atoms are suggested to be possibly converted to perfluorooctanoic acid or perfluorocarboxylic acids having more than eight carbon atoms by biodegradation or chemical degradation in the environment, and there is concern that it will be difficult to produce and use those compounds for the future. However, compounds containing a perfluoroalkyl group having six or less carbon atoms are said to have low bioaccumulation potential.

DISCLOSURE OF THE INVENTION

Problems to be Solved by the Invention

An object of the present invention is to provide a mixture of fluoroalkyl alcohols that are compounds containing a perfluoroalkyl group having six or less carbon atoms, which is expected to have low bioaccumulation potential, and having a CH=CF group vulnerable to biodegradation (biochemical degradation by microorganisms) or chemical degradation (degradation by acids, bases, active oxygen, ozone, etc., in the environment) formed in the fluoroalkyl group, and that can be effectively used as surfactants, etc.; and to provide a method for producing such a fluoroalkyl alcohol mixture.

Means for Solving the Problems

The present invention provides a mixture of fluoroalkyl alcohols represented by the general formulae:

$$CF_3(CF_2)_n(CH=CF)_a(CF_2CF_2)_b(CH_2CH_2)_cOH \quad [Ia]$$

and $$CF_3(CF_2)_{n-1}(CF=CH)_aCF_2(CF_2CF_2)_b(CH_2CH_2)_cOH \quad [Ib]$$

wherein n is an integer of 1 to 5, a is an integer of 1 to 4, b is an integer of 0 to 3, and c is an integer of 1 to 3.

This fluoroalkyl alcohol mixture is produced by the reaction of a fluoroalkyl iodide represented by the general formula:

$$CF_3(CF_2)_n(CH_2CF_2)_a(CF_2CF_2)_b(CH_2CH_2)_cI \quad [II]$$

with N-methylformamide, followed by hydrolysis in the presence of a basic compound. Here, the $CH_2CF_2$ and $CF_2CF_2$ groups can be randomly bonded in the formula [II]; however, at least one $CH_2CF_2$ group must be adjacent to the $CF_3(CF_2)_n$ group.

Effect of the Invention

In the fluoroalkyl alcohol mixture of the present invention, the $CH_2CF_2$ group derived from vinylidene fluoride in the molecule easily undergoes HF-elimination to form a double bond, which is vulnerable to degradation as a result of ozone decomposition; therefore, the perfluoroalkyl group can be decomposed into a group having six or less carbon atoms, which is expected to have low bioaccumulation potential. Moreover, similar to conventional compounds, the fluoroalkyl alcohol mixture can be effectively used as a surfactant, and a mixture of a (meth)acrylic acid derivative thereof can be effectively used as a monomer for synthesizing a water- and oil-repellent.

BEST MODE FOR CARRYING OUT THE INVENTION

The fluoroalkyl iodide of the formula:

$$CH_3(CF_2)_n(CH_2CF_2)_a(CF_2CF_2)_b(CH_2CH_2)_cI \quad [II],$$

which is used as a starting material for the production of the fluoroalkyl alcohol mixture, is produced by the addition reaction of a terminally iodized compound represented by the general formula:

$$CF_3(CF_2)_n(CH_2CF_2)_a(CF_2CF_2)_bI \quad [A]$$

with ethylene. The ethylene addition reaction is carried out in such a manner that Compound [A] is subjected to an addition reaction with pressurized ethylene in the presence of a peroxide initiator. The number of addition is 1 or more, and preferably 1, although depending on the reaction conditions. Although the reaction temperature depends on the degradation temperature of the initiator used, the reaction is generally conducted at about 80 to 120° C.; when a peroxide initiator that decomposes at a low temperature is used, the reaction can be conducted at 80° C. or less. As a peroxide initiator, tert-butyl peroxide, di(tert-butylcyclohexyl)peroxydicarbonate, dicetyl peroxydicarbonate, or the like may be used at a ratio of about 1 to 5 mol % based on the amount of Compound [A].

Specifically, Compound [A] is represented by the general formula:

$$CF_3(CF_2)_n(CH_2CF_2)_{s+p}(CF_2CF_2)_{t+r}I \quad [A']$$

p: the number of vinylidene fluoride skeletons added by reaction r: the number of tetrafluoroethylene skeletons added by reaction s+p: the same as "a" defined above (1 to 4, preferably 1 to 2)

t+r: the same as "b" defined above (0 to 3, preferably 1 to 2)

More specifically, Compound [A] can be produced by any of the following methods.

(1) A Perfluoroalkyl Iodide Represented by the General Formula:

$$CF_3(CF_2)_nI \quad [B-1],$$

wherein n is an integer of 1 to 5, is reacted with vinylidene fluoride in the presence of a peroxide initiator to produce a terminally iodized polyfluoroalkane oligomer represented by the general formula:

$$CF_3(CF_2)_n(CH_2CF_2)_pI \quad [A-1],$$

wherein n is as defined above, and p is an integer of 1 to 4, indicating the number of vinylidene fluoride skeletons added by reaction.

(2) A Terminally Iodized Polyfluoroalkane Represented by the General Formula:

$$CF_3(CF_2)_n(CH_2CF_2)_s(CF_2CF_2)_tI \quad [B-2],$$

wherein n is an integer of 1 to 5, s is an integer of 1 to 4, indicating the number of vinylidene fluoride skeletons in the starting material, and t is an integer of 0 to 2, indicating the number of tetrafluoroethylene skeletons in the starting material; is reacted with tetrafluoroethylene in the presence of a peroxide initiator to produce a terminally iodized polyfluoroalkane oligomer represented by the general formula:

$$CF_3(CF_2)_n(CH_2CF_2)_s(CF_2CF_2)_{t+r}I \quad [A-2],$$

wherein n, s, and t are as defined above, and r is an integer of 1 to 3, indicating the number of tetrafluoroethylene skeletons added by reaction.

(3) A Terminally Iodized Polyfluoroalkane Represented by the General Formula:

$$CF_3(CF_2)_n(CH_2CF_2)_s(CF_2CF_2)_tI \quad [B-3],$$

wherein n is an integer of 1 to 5, s is an integer of 1 to 3, indicating the number of vinylidene fluoride skeletons in the starting material, and t is an integer of 1 to 3, indicating the number of tetrafluoroethylene skeletons in the starting material; is reacted with vinylidene fluoride in the presence of a peroxide initiator to produce a terminally iodized polyfluoroalkane oligomer represented by the general formula:

$$CF_3(CF_2)_s(CH_2CF_2)_{s+p}(CF_2CF_2)_tI \quad [A-3],$$

wherein n, s, and t are as defined above, and p is an integer of 1 to 3, indicating the number of vinylidene fluoride skeletons added by reaction.

Specific examples of terminally iodized polyfluoroalkanes usable in the present invention include the following compounds:

$CF_3(CF_2)(CH_2CF_2)I$
$CF_3(CF_2)(CH_2CF_2)_2I$
$CF_3(CF_2)_2(CH_2CF_2)I$
$CF_3(CF_2)_2(CH_2CF_2)_2I$
$CF_3(CF_2)_3(CH_2CF_2)I$
$CF_3(CF_2)_3(CH_2CF_2)_2I$
$CF_3(CF_2)(CH_2CF_2)(CF_2CF_2)I$
$CF_3(CF_2)(CH_2CF_2)(CF_2CF_2)_2I$
$CF_3(CF_2)_2(CH_2CF_2)(CF_2CF_2)I$
$CF_3(CF_2)_2(CH_2CF_2)(CF_2CF_2)_2I$
$CF_3(CF_2)_3(CH_2CF_2)_2(CF_2CF_2)I$
$CF_3(CF_2)_3(CH_2CF_2)_2(CF_2CF_2)_2I$

The oligomerization reaction of the perfluoroalkyl iodide or terminally iodized polyfluoroalkane of the formula [B-1], [B-2], or [B-3] with vinylidene fluoride or tetrafluoroethylene is carried out in the presence of a peroxide initiator, such as di(tert-butylcyclohexyl) peroxydicarbonate, dicetyl peroxydicarbonate, etc. A peroxide initiator is used at a ratio of about 0.1 to 0.5 mol % based on the amount of Compound [B-1], [B-2], or [B-3], and p and r indicate the increased degree of oligomerization of vinylidene fluoride or tetrafluoroethylene, respectively. Although the reaction temperature depends on the degeneration temperature of the initiator used, the reaction can be carried out at 80° C. or less by using a peroxide initiator that decomposes at a low temperature.

The fluoroalkyl iodide [II] is reacted with N-methylformamide, followed by hydrolysis in the presence of a basic compound, thereby forming a mixture of fluoroalkyl alcohols represented by the general formulae:

$$CF_3(CF_2)_n(CH=CF)_a(CF_2CF_2)_b(CH_2CH_2)_cOH \quad [Ia]$$

and $$CF_3(CF_2)_{n-1}(CF=CH)_aCF_2(CF_2CF_2)_b(CH_2CH_2)_cOH \quad [Ib]$$

Here, the mixture of Compounds [Ia] and [Ib] is formed because in the HF-elimination reaction, the elimination of the H atom of the methylene chain $CH_2$ and the F atom of either one of the fluoromethylene chains $CF_2$ bonding back and forth to the $CH_2$ occurs equally in the anteroposterior position. Moreover, since the HF-elimination reactions are equivalent, the proportion of the produced Compounds [Ia] and [Ib] is approximately 1:1. Although Compounds [Ia] and [Ib] cannot be separately identified because they are very similar constitutional isomers, a mixture of these compounds can be directly used as a synthetic starting material of other substances because they have equivalent reactivity.

This reaction is carried out by reacting the fluoroalkyl iodide [II] with N-methylformamide in an amount of about 5 to 20 times by mole, and preferably about 10 to 15 times by mole, based on the amount of fluoroalkyl iodide [II] at about 140 to 160° C. for about 7 to 10 hours, followed by a reaction with a basic compound such as sodium hydroxide, potassium hydroxide, etc. at about 85 to 95° C. for about 7 to 10 hours.

The obtained mixture of fluoroalkyl alcohols [Ia] and [Ib] can be subjected to an esterification reaction with acrylic acid or methacrylic acid. The esterification reaction is conducted as follows: An aromatic hydrocarbon solvent such as toluene, benzene, etc., a catalyst such as p-toluenesulfonic acid, etc., and hydroquinone, which is used as a polymerization inhibitor, are added to the fluoroalkyl alcohol mixture, followed by heating at about 90 to 100° C. Then, about 1 to 2 times by mole of acrylic acid or methacrylic acid is added, and the resultant mixture is heated at about 110 to 120° C. for about 2 to 5 hours, followed by dehydration and esterification reaction.

EXAMPLES

The following describes the present invention with reference to examples.

Reference Example 1

A compound of the formula: $CF_3(CF_2)_3(CH_2CF_2)(CF_2CF_2)_2I$ (99 GC %) (603 g; 0.99 mol) and 7 g of di-tert-butyl peroxide were charged in a 1200-ml autoclave equipped with a stirrer and thermometer, and the autoclave was degassed by a vacuum pump. After the internal temperature was raised to 80° C., ethylene was sequentially introduced so that the internal pressure was 0.5 MPa. When the internal pressure decreased to 0.2 MPa, ethylene was introduced again to return the pressure to 0.5 MPa; this operation was repeated. While maintaining the internal temperature at 80 to 115° C., 41 g (1.45 mol) of ethylene was introduced over about 3 hours. The content was collected at an internal temperature of 50° C. or less, thereby obtaining 637 g of compound of the formula: $CF_3(CF_2)_3(CH_2CF_2)(CF_2CF_2)_2(CH_2CH_2)I$ (98 GC %) (yield: 98.8%).

Example 1

The compound of the formula: $CF_3(CF_2)_3(CH_2CF_2)(CF_2CF_2)_2(CH_2CH_2)I$ (98 GC %) (150 g; 0.23 mol) obtained in Reference Example 1 and 170 g (2.88 mol) of N-methylformamide were charged in a four-necked 300-ml flask equipped with a condenser, thermometer, and stirrer, and the mixture was stirred and reacted at 150° C. for 8 hours. After the completion of the reaction, the reaction mixture was washed with 100 ml of water, and 133 g of lower layer of the mixture was mixed with 140 g of a 10 wt. % NaOH aqueous solution, followed by reaction under stirring at 90° C. for 8 hours. After the reaction mixture was allowed to stand, 124 g of reaction product (66.4 GC %), which was light-yellow, transparent liquid at ambient temperature, was obtained as the lower layer of the mixture (yield: 70.5%).

The reaction product was subjected to distillation under reduced pressure under conditions where the internal pressure was 0.2 kPa, the internal temperature was 109 to 123° C., and the overhead temperature was 86 to 87° C. Thus, 30 g of purified reaction product (97.4 GC %) was obtained (distillation yield: 35.6%). The results of $^1$H-NMR and $^{19}$F-NMR confirmed that this purified reaction product was a mixture of compounds represented by the following formulae:

$CF_3(CF_2)_3(CH=CF)(CF_2CF_2)_2(CH_2CH_2)OH$ $CF_3(CF_2)_2(CF=CH)CF_2(CF_2CF_2)_2(CH_2CH_2)OH$ $^1$H-NMR (CDCl$_3$, TMS):
δ5.71-5.92 (CH=CF, CF=CH)
2.28-2.45 (CH$_2$CH$_2$)
3.97(CH$_2$CH$_2$)
2.28-2.45(OH)
$^{19}$F-NMR(CDCl$_3$, C$_6$F$_6$):
ppm −82.13 to −81.77 (CF$_3$)
−128.22 to −126.84 (CF$_3$CF$_2$CF$_2$)
−125.52 to −124.83 (CF$_3$CF$_2$CF$_2$)
−111.22 to −109.58 (CF$_2$CH=CF, CF=CHCF$_2$)
−120.76 to −119.73 (CF$_2$CF$_2$CF$_2$CF$_2$CH$_2$)
−123.69 to −122.27 (CF$_2$CF$_2$CF$_2$CF$_2$CH$_2$)
−114.44 (CF$_2$CF$_2$CF$_2$CF$_2$CH$_2$)
−124.73 (CF$_2$CF$_2$CF$_2$CF$_2$CH$_2$)

Reference Example 2

The mixture of compounds (97.4 GC %) obtained in Example 1 (30.0 g; 0.06 mol), 21 g of toluene, 6 g of p-toluenesulfonic acid, and 0.3 g of hydroquinone were charged in a four-necked 100-ml flask equipped with a condenser, thermometer, and stirrer. After the internal temperature was raised to 100° C., 5 g (0.07 mol) of acrylic acid was added, and the mixture was stirred for reaction at an internal temperature of 115° C. for 4 hours. After the completion of the reaction, the toluene was removed by an evaporator from 61 g of the reaction mixture solution obtained by cooling, and 42 g of residue was washed with tap water. Thus, 34 g of reaction product (86.9 GC %), which was light-yellow, transparent liquid at ambient temperature, was obtained (yield: 84.1%).

The reaction product was subjected to distillation under reduced pressure under conditions where the internal pressure was 0.1 kPa, the internal temperature was 128 to 133° C., and the overhead temperature was 64 to 72° C. Thus, 23 g of purified reaction product (98.0 GC %) was obtained (distillation yield: 77.7%). The results of $^1$H-NMR and $^{19}$F-NMR confirmed that this purified reaction product was a mixture of compounds represented by the following formulae:

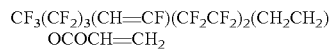
$CF_3(CF_2)_3(CH=CF)(CF_2CF_2)_2(CH_2CH_2)OCOCH=CH_2$

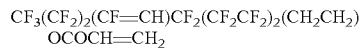
$CF_3(CF_2)_2(CF=CH)CF_2(CF_2CF_2)_2(CH_2CH_2)OCOCH=CH_2$ $^1$H-NMR (CDCl$_3$, TMS):
δ5.73-5.97 (CH=CF, CF=CH)
2.48 (CH$_2$CH$_2$)
4.46 (CH$_2$CH$_2$)
6.14 (CH=CH$_2$)
6.41, 5.73-5.97 (CH=CH$_2$)
$^{19}$F-NMR (CDCl$_3$, C$_6$F$_6$):
ppm −82.06 to −81.73 (CF$_3$)
−128.22 to −126.84 (CF$_3$CF$_2$CF$_2$)
−125.52 to −124.81 (CF$_3$CF$_2$CF$_2$)
−111.22 to −109.58 (CF$_2$CH=CF, CF=CHCF$_2$)
−120.76 to −119.73 (CF$_2$CF$_2$CF$_2$CF$_2$CH$_2$)
−123.69 to −122.27 (CF$_2$CF$_2$CF$_2$CF$_2$CH$_2$)
−114.54 (CF$_2$CF$_2$CF$_2$CF$_2$CH$_2$)
−124.56 (CF$_2$CF$_2$CF$_2$CF$_2$CH$_2$)

Reference Example 3

A compound of the formula: $CF_3(CF_2)_3(CH_2CF_2)(CF_2CF_2)I$ (99.3 GC %) (609 g; 1.19 mol) and 6 g of di-tert-butyl peroxide were charged in a 1200-ml autoclave equipped with a stirrer and thermometer, and the autoclave was degassed by a vacuum pump. After the internal temperature was raised to 80° C., ethylene was sequentially introduced so that the internal pressure was 0.5 MPa. When the internal pressure decreased to 0.2 MPa, ethylene was introduced again to return the pressure to 0.5 MPa; this operation was repeated. While maintaining the internal temperature at 80 to 115° C., 50 g (1.79 mol) of ethylene was introduced over about 3 hours. The content was collected at an internal temperature of 50° C. or less, thereby obtaining 640 g of compound of the formula: $CF_3(CF_2)_3(CH_2CF_2)(CF_2CF_2)(CH_2CH_2)I$ (97.4 GC %) (yield: 97.3%).

Example 2

The compound of the formula: $CF_3(CF_2)_3(CH_2CF_2)(CF_2CF_2)(CH_2CH_2)I$ (97.4 GC %) (153 g; 0.28 mol) obtained in Reference Example 3 and 207 g (3.51 mol) of N-methylformamide were charged in a four-necked 300-ml flask equipped with a condenser, thermometer, and stirrer, and the mixture was stirred and reacted at 150° C. for 8 hours. After the completion of the reaction, the reaction mixture was washed with 100 ml of water, and 135 g of lower layer of the mixture was mixed with 140 g of a 10 wt. % NaOH aqueous solution, followed by reaction under stirring at 90° C. for 8 hours. After the reaction mixture was allowed to stand, 132 g of reaction product (65.3 GC %), which was light-yellow, transparent liquid at ambient temperature, was obtained as the lower layer of the mixture (yield: 75.4%).

The reaction product was subjected to distillation under reduced pressure under conditions where the internal pressure was 0.2 kPa, the internal temperature was 103 to 108° C., and the overhead temperature was 84 to 85° C. Thus, 38 g of purified reaction product (97.8 GC %) was obtained (distillation yield: 42.8%). The results of $^1$H-NMR and $^{19}$F-NMR confirmed that this purified reaction product was a mixture of compounds represented by the following formulae:

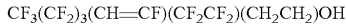
$CF_3(CF_2)_3(CH=CF)(CF_2CF_2)(CH_2CH_2)OH$

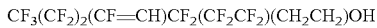
$CF_3(CF_2)_2(CF=CH)CF_2(CF_2CF_2)(CH_2CH_2)OH$ $^1$H-NMR (CDCl$_3$, TMS):
δ 5.75-5.88 (C$\underline{H}$=CF, CF=C$\underline{H}$)
2.35 (CH$_2$C$\underline{H_2}$)
3.93 (C$\underline{H_2}$CH$_2$)
3.07-3.28 (O$\underline{H}$)
$^{19}$F-NMR (C$\underline{D}$Cl$_3$, C$_6$F$_6$):
ppm −82.0 to −81.6 (CF$_3$)
−128.0 to −126.6 (CF$_3$$\overline{C}$F$_2$CF$_2$)
−125.3 to −124.6 (CF$_3$C$\overline{F_2}$CF$_2$)
−111.1 to −108.8 (CF$_2$C$\underline{H}$=$\overline{C}$F, C$\underline{F}$=CHCF$_2$)
−126.6 (CF$_2$CF$_2$C$\underline{H_2}$)
−113.2 (C$\overline{F_2}$C$\underline{F_2}$CH$_2$)

Reference Example 4

The mixture of compounds (97.8 GC %) obtained in Example 2 (37 g; 0.09 mol), 23 g of toluene, 7 g of p-toluenesulfonic acid, and 0.4 g of hydroquinone were charged in a four-necked 100-ml flask equipped with a condenser, thermometer, and stirrer. After the internal temperature was raised to 100° C., 8 g (0.11 mol) of acrylic acid was added, and the mixture was stirred for reaction at an internal temperature of 115° C. for 4 hours. After the completion of the reaction, the toluene was removed by an evaporator from 74 g of the reaction mixture solution obtained by cooling, and 53 g of residue was washed with tap water. Thus, 42 g of reaction product (88.1 GC %), which was light-yellow, transparent liquid at ambient temperature, was obtained (yield: 85.4%).

The reaction product was subjected to distillation under reduced pressure under conditions where the internal pressure was 0.1 kPa, the internal temperature was 124 to 128° C., and the overhead temperature was 63 to 68° C. Thus, 30 g of purified reaction product (99.2 GC %) was obtained (distillation yield: 79.2%). The results of $^1$H-NMR and $^{19}$F-NMR confirmed that this purified reaction product was a mixture of compounds represented by the following formulae:

$CF_3(CF_2)_3(CH=CF)(CF_2CF_2)(CH_2CH_2)$
   $OCOCH=CH_2$ $CF_3(CF_2)_2(CF=CH)CF_2(CF_2CF_2)(CH_2CH_2)$
   $OCOCH=CH_2$ $^1$H-NMR (CDCl$_3$, TMS):
δ 5.75-5.88 (C$\underline{H}$=CF, CF=C$\underline{H}$)
2.52 (CH$_2$C$\underline{H_2}$)
4.46 (C$\underline{H_2}$CH$_2$)
6.13 (CH=$\overline{C}$H$_2$)
6.41, 5.$\overline{89}$ (CH=C$\underline{H_2}$)
$^{19}$F-NMR (CDCl$_3$, $\overline{C_6}$F$_6$):
ppm −82.0 to −81.7 (CF$_3$)
−127.9 to −126.5 (CF$_3$$\overline{C}$F$_2$CF$_2$)
−125.4 to −124.8 (CF$_3$C$\overline{F_2}$CF$_2$)
−110.9 to −110.2 (CF$_2$C$\underline{H}$=$\overline{C}$F, C$\underline{F}$=CHCF$_2$)
−126.7 (CF$_2$CF$_2$C$\underline{H_2}$)
−113.7 (C$\overline{F_2}$C$\underline{F_2}$CH$_2$)

Reference Example 5

A compound of the formula: $CF_3CF_2(CH_2CF_2)(CF_2CF_2)_3$I (98.7 GC %) (605 g: 0.98 mol) and 7 g of di-tert-butyl peroxide were charged in a 1200-ml autoclave equipped with a stirrer and thermometer, and the autoclave was degassed by a vacuum pump. After the internal temperature was raised to 80° C., ethylene was sequentially introduced so that the internal pressure was 0.5 MPa. When the internal pressure decreased to 0.2 MPa, ethylene was introduced again to return the pressure to 0.5 MPa; this operation was repeated. While maintaining the internal temperature at 80 to 115° C., 43 g (1.53 mol) of ethylene was introduced over about 3 hours. The content was collected at an internal temperature of 50° C. or less, thereby obtaining 630 g of compound of the formula: $CF_3CF_2(CH_2CF_2)(CF_2CF_2)_3(CH_2CH_2)I$ (97.7 GC %) (yield: 98.5% of).

Example 3

The compound of the formula: $CF_3CF_2(CH_2CF_2)$ $(CF_2CF_2)_3(CH_2CH_2)I$ (97.7 GC %) (150 g; 0.23 mol) obtained in Reference Example 5 and 170 g (2.88 mol) of N-methylformamide were charged in a four-necked 300-ml flask equipped with a condenser, thermometer, and stirrer, and the mixture was stirred and reacted at 150° C. for 8 hours. After the completion of the reaction, the reaction mixture was washed with 100 ml of water, and 132 g of lower layer of the mixture was mixed with 141 g of a 10 wt. % NaOH aqueous solution, followed by reaction under stirring at 90° C. for 8 hours. After the reaction mixture was allowed to stand, 126 g of reaction product (66.1 GC %), which was light-yellow, transparent liquid at ambient temperature, was obtained as the lower layer of the mixture (yield: 71.4%).

The reaction product was subjected to distillation under reduced pressure under conditions where the internal pressure was 0.2 kPa, the internal temperature was 110 to 123° C., and the overhead temperature was 85 to 87° C. Thus, 31 g of purified reaction product (97.5 GC %) was obtained (distillation yield: 35.9%). The results of $^1$H-NMR and $^{19}$F-NMR confirmed that this purified reaction product was a mixture of compounds represented by the following formulae:

$CF_3CF_2(CH=CF)(CF_2CF_2)_3(CH_2CH_2)OH$

$CF_3(CF=CH)CF_2(CF_2CF_2)_3(CH_2CH_2)OH$ $^1$H-NMR (CDCl$_3$, TMS):
δ 5.13-5.84 (C$\underline{H}$=CF, CF=C$\underline{H}$)
2.28-2.45 (C$\underline{H_2}$CH$_2$)
3.97 (CH$_2$C$\underline{H_2}$)
2.27-2.47 (O$\underline{H}$)
$^{19}$F-NMR (C$\overline{D}$Cl$_3$, C$_6$F$_6$):
ppm −87.1 to −86.7 (CF$_3$)
−118.1 to −109.7 (CF$_2$C$\underline{H}$=CF, CF=CHCF$_2$)
−120.8 to −119.6 (C$\overline{F_2}$CF$_2$CF$_2$$\overline{C}$F$_2$$\overline{C}$F$_2$CF$_2$C$\overline{H_2}$)
−120.4 to −119.3 (C$\overline{F_2}$CF$_2$CF$_2$CF$_2$CF$_2$CF$_2$CH$_2$)
−120.4 to −119.3 (CF$_2$C$\overline{F_2}$CF$_2$CF$_2$CF$_2$CF$_2$CH$_2$)
−123.4 to −122.1 (CF$_2$CF$_2$C$\overline{F_2}$CF$_2$CF$_2$CF$_2$CH$_2$)
−124.6 (CF$_2$CF$_2$CF$_2$CF$_2$CF$_2$CF$_2$C$\underline{H_2}$)
−114.6 (CF$_2$CF$_2$CF$_2$CF$_2$C$\overline{F_2}$C$\underline{F_2}$CH$_2$)

Reference Example 6

The mixture of compounds (97.5 GC %) obtained in Example 3 (30.0 g; 0.06 mol), 21 g of toluene, 6 g of p-toluenesulfonic acid, and 0.3 g of hydroquinone were charged in a four-necked 100-ml flask equipped with a condenser, thermometer, and stirrer. After the internal temperature was raised to 100° C., 5 g (0.07 mol) of acrylic acid was added, and the mixture was stirred for reaction at an internal temperature of 115° C. for 4 hours. After the completion of the reaction, the toluene was removed by an evaporator from 61 g of the reaction mixture solution obtained by cooling, and 42 g of

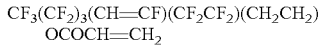

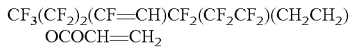

residue was washed with tap water. Thus, 34 g of reaction product (87.3 GC %), which was light-yellow, transparent liquid at ambient temperature, was obtained (yield: 84.7%).

The reaction product was subjected to distillation under reduced pressure under conditions where the internal pressure was 0.1 kPa, the internal temperature was 129 to 133° C., and the overhead temperature was 65 to 72° C. Thus, 24 g of purified reaction product (99.3 GC %) was obtained (distillation yield: 78.3%). The results of $^1$H-NMR and $^{19}$F-NMR confirmed that this purified reaction product was a mixture of compounds represented by the following formulae:

$CF_3CF_2(CH=CF)(CF_2CF_2)_3(CH_2CH_2)OCOCH=CH_2$

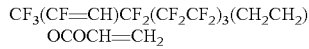

$CF_3(CF=CH)CF_2(CF_2CF_2)_3(CH_2CH_2)OCOCH=CH_2$ $^1$H-NMR (CDCl$_3$, TMS):
δ5.72-5.85 (C$\underline{H}$=CF, CF=C$\underline{H}$)
2.51 (CH$_2$C$\underline{H_2}$)
4.46 (C$\underline{H_2}$CH$_2$)
6.13 (CH=C$\underline{H_2}$)
6.41, 5.89 (C$\underline{H}$=CH$_2$)
$^{19}$F-NMR (CDCl$_3$, C$_6$F$_6$):
ppm −87.0 to −86.7 (CF$_3$)
−117.6 to −110.4 (CF$_2$C$\underline{H}$=CF, CF=C$\underline{H}$CF$_2$)
−121.7 to −119.9 (C$\underline{F_2}$CF$_2$CF$_2$CF$_2$CF$_2$CF$_2$C$\underline{H_2}$)
−120.9 to −120.0 (CF$_2$C$\underline{F_2}$CF$_2$CF$_2$CF$_2$CF$_2$CH$_2$)
−120.9 to −120.0 (CF$_2$CF$_2$C$\underline{F_2}$CF$_2$CF$_2$CF$_2$CH$_2$)
−123.3 to −122.0 (CF$_2$CF$_2$C$\underline{F_2}$CF$_2$CF$_2$CF$_2$CH$_2$)
−124.4 (CF$_2$CF$_2$CF$_2$CF$_2$C$\underline{F_2}$CF$_2$C$\underline{H_2}$)
−114.5 (CF$_2$CF$_2$CF$_2$CF$_2$C$\underline{F_2}$CF$_2$CH$_2$)

Reference Example 7

A compound of the formula: CF$_3$CF$_2$(CH$_2$CF$_2$)(CF$_2$CF$_2$)$_2$I (99.4 GC %) (605 g; 1.18 mol) and 6 g of di-tert-butyl peroxide were charged in a 1200-ml autoclave equipped with a stirrer and thermometer, and the autoclave was degassed by a vacuum pump. After the internal temperature was raised to 80° C., ethylene was sequentially introduced so that the internal pressure was 0.5 MPa. When the internal pressure decreased to 0.2 MPa, ethylene was introduced again to return the pressure to 0.5 MPa; this operation was repeated. While maintaining the internal temperature at 80 to 115° C., 50 g (1.79 mol) of ethylene was introduced over about 3 hours. At an internal temperature of 50° C. or less, the content was collected, thereby obtaining 639 g of compound of the formula: CF$_3$CF$_2$(CH$_2$CF$_2$)(CF$_2$CF$_2$)$_2$(CH$_2$CH$_2$)I (97.3 GC %) (yield: 98.0%).

Example 4

The compound of the formula: CF$_3$CF$_2$(CH$_2$CF$_2$)(CF$_2$CF$_2$)$_2$(CH$_2$CH$_2$)I (97.3 GC %) (150 g; 0.27 mol) obtained in Reference Example 7 and 205 g (3.48 mol) of N-methylformamide were charged in a four-necked 300-ml flask equipped with a condenser, thermometer, and stirrer, and the mixture was stirred and reacted at 150° C. for 8 hours. After the completion of the reaction, the reaction mixture was washed with 100 ml of water, and 134 g of lower layer of the mixture was mixed with 140 g of a 10 wt. % NaOH aqueous solution, followed by reaction under stirring at 90° C. for 8 hours. After the reaction mixture was allowed to stand, 127 g of reaction product (67.1 GC %), which was light-yellow transparent liquid at ambient temperature, was obtained as the lower layer of the mixture (yield: 77.1%).

The reaction product was subjected to distillation under reduced pressure under conditions where the internal pressure was 0.2 kPa, the internal temperature was 104 to 119° C., and the overhead temperature was 84 to 85° C. Thus, 36 g of purified reaction product (98.0GC%) was obtained (distillation yield: 41.6%). The results of $^1$H-NMR and $^{19}$F-NMR confirmed that this purified reaction product was a mixture of compounds represented by the following formulae:

$CF_3CF_2(CH=CF)(CF_2CF_2)_2(CH_2CH_2)OH$

$CF_3(CF=CH)CF_2(CF_2CF_2)_2(CH_2CH_2)OH$ $^1$H-NMR (CDCl$_3$, TMS):
δ5.11-5.81 (C$\underline{H}$=CF, CF=C$\underline{H}$)
2.26-2.42 (C$\underline{H_2}$CH$_2$)
3.95 (CH$_2$C$\underline{H_2}$)
3.02-3.21 (O$\underline{H}$)
$^{19}$F-NMR (CDCl$_3$, C$_6$F$_6$):
ppm −87.0 to −86.6 (CF$_3$)
−118.0 to −109.6 (CFC$\underline{H}$=CF, CF=C$\underline{H}$CF$_2$)
−120.1 to −119.3 (C$\underline{F_2}$CF$_2$CF$_2$CF$_2$CH$_2$)
−123.4 to −122.1 (CF$_2$C$\underline{F_2}$CF$_2$CF$_2$CH$_2$)
−124.6 (CF$_2$CF$_2$CF$_2$C$\underline{F_2}$CH$_2$)
−114.2 (CF$_2$CF$_2$C$\underline{F_2}$CF$_2$CH$_2$)

Reference Example 8

The mixture of compounds (98.0 GC %) obtained in Example 4 (35 g; 0.08 mol), 22 g of toluene, 7 g of p-toluenesulfonic acid, and 0.4 g of hydroquinone were charged in a four-necked 100-ml flask equipped with a condenser, thermometer, and stirrer. After the internal temperature was raised to 100° C., 8 g (0.11 mol) of acrylic acid was added, and the mixture was stirred for reaction at an internal temperature of 115° C. for 4 hours. After the completion of the reaction, the toluene was removed by an evaporator from 72 g of the reaction mixture solution obtained by cooling, and 52 g of residue was washed with tap water. Thus, 42 g of reaction product (87.9 GC %), which was a light-yellow, transparent liquid at ambient temperature, was obtained (yield: 85.8%).

The reaction product was subjected to distillation under reduced pressure under conditions where the internal pressure was 0.1 kPa, the internal temperature was 124 to 128° C., and the overhead temperature was 63 to 68° C. Thus, 30 g of purified reaction product (98.8 GC %) was obtained (distillation yield: 79.1%). The results of $^1$H-NMR and $^{19}$F-NMR confirmed that this purified reaction product was a mixture of compounds represented by the following formulae:

$CF_3CF_2(CH=CF)(CF_2CF_2)_2(CH_2CH_2)OCOCH=CH_2$

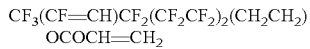

$CF_3(CF=CH)CF_2(CF_2CF_2)_2(CH_2CH_2)OCOCH=CH_2$ $^1$H-NMR (CDCl$_3$, TMS):
δ5.70-5.83 (C$\underline{H}$=CF, CF=C$\underline{H}$)
2.46 (CH$_2$C$\underline{H_2}$)
4.43 (C$\underline{H_2}$CH$_2$)
6.14 (CH=C$\underline{H_2}$)
6.41, 5.8 (C$\underline{H}$=CH$_2$)
$^{19}$F-NMR (CDCl$_3$, C$_6$F$_6$):
ppm −87.0 to −86.7 (CF$_3$)
−117.6 to −110.4 (CF$_2$C$\underline{H}$=CF, CF=C$\underline{H}$CF$_2$)
−122.1 to −120.3 (C$\underline{F_2}$CF$_2$CF$_2$CF$_2$C$\underline{H_2}$)
−123.8 to −122.5 (C$\underline{F_2}$CF$_2$CF$_2$CF$_2$CH$_2$)

−124.8 (CF$_2$CF$_2$CF$_2$CF$_2$CH$_2$)
−114.5 (CF$_2$CF$_2$CF$_2$CF$_2$CH$_2$)

Reference Example 9

A compound of the formula: CF$_3$CF$_2$(CH$_2$CF$_2$)(CF$_2$CF$_2$)I (99.8 GC %) (610 g; 1.48 mol) and 7 g of di-tert-butyl peroxide were charged in a 1200-ml autoclave equipped with a stirrer and thermometer, and the autoclave was degassed by a vacuum pump. After the internal temperature was raised to 80° C., ethylene was sequentially introduced so that the internal pressure was 0.5 MPa. When the internal pressure decreased to 0.2 MPa, ethylene was introduced again to return the pressure to 0.5 MPa; this operation was repeated. While maintaining the internal temperature at 80 to 115° C., 62 g (2.23 mol) of ethylene was introduced over about 3 hours. The content was collected at an internal temperature of 50° C. or less, thereby obtaining 644 g of compound of the formula: CF$_3$CF$_2$(CH$_2$CF$_2$)(CF$_2$CF$_2$)(CH$_2$CH$_2$)I (98.7 GC %) (yield: 98.0%).

Example 5

The compound of the formula: CF$_3$CF$_2$(CH$_2$CF$_2$)(CF$_2$CF$_2$)(CH$_2$CH$_2$)I (98.7 GC %) (150 g; 0.34 mol) obtained in Reference Example 9 and 251 g (4.26 mol) of N-methylformamide were charged in a four-necked 300-ml flask equipped with a condenser, thermometer, and stirrer, and the mixture was stirred and reacted at 150° C. for 8 hours. After the completion of the reaction, the reaction mixture was washed with 100 ml of water, and 130 g of lower layer of the mixture was mixed with 135 g of a 10 wt. % NaOH aqueous solution, followed by reaction under stirring at 90° C. for 8 hours. After the reaction mixture was allowed to stand, 119 g of reaction product (68.8 GC %), which was light-yellow, transparent liquid at ambient temperature, was obtained as the lower layer of the mixture (yield: 78.2%).

The reaction product was subjected to distillation under reduced pressure under conditions where the internal pressure was 0.2 kPa, the internal temperature was 100 to 114° C., and the overhead temperature was 80 to 81° C. Thus, 38 g of purified reaction product (98.1 GC %) was obtained (distillation yield: 45.3%). The results of $^1$H-NMR and $^{19}$F-NMR confirmed that this purified reaction product was a mixture of compounds represented by the following formulae:

CF$_3$CF$_2$(CH=CF)(CF$_2$CF$_2$)(CH$_2$CH$_2$)OH

CF$_3$(CF=CH)CF$_2$(CF$_2$CF$_2$)(CH$_2$CH$_2$)OH $^1$H-NMR (CDCl$_3$, TMS):
δ5.09-5.77 (CH=CF, CF=CH)
2.21-2.36 (CH$_2$CH$_2$) 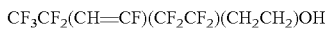
3.91 (CH$_2$CH$_2$) 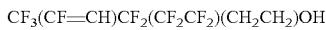
3.55-3.68 (OH)
$^{19}$F-NMR (CDCl$_3$, C$_6$F$_6$):
ppm −87.0 to −86.6 (CF$_3$)
−118.0 to −109.5 (CF$_2$CH=CF, CF=CHCF$_2$)
−124.6 (CF$_2$CF$_2$CH$_2$)
−114.2 (CF$_2$CF$_2$CH$_2$)

Reference Example 10

The mixture of compounds (98.1 GC %) obtained in Example 5 (37 g; 0.12 mol), 26 g of toluene, 8 g of p-toluenesulfonic acid, and 0.4 g of hydroquinone were charged in a four-necked 100-ml flask equipped with a condenser, thermometer, and stirrer. After the internal temperature was raised to 100° C., 11 g (0.15 mol) of acrylic acid was added, and the mixture was stirred for reaction at an internal temperature of 115° C. for 4 hours. After the completion of the reaction, the toluene was removed by an evaporator from 81 g of the reaction mixture solution obtained by cooling, and 58 g of residue was washed with tap water. Thus, 45 g of reaction product (89.2 GC %), which was light-yellow, transparent liquid at ambient temperature, was obtained (yield: 87.5%).

The reaction product was subjected to distillation under reduced pressure under conditions where the internal pressure was 0.1 kPa, the internal temperature was 120 to 124° C., and the overhead temperature was 59 to 63° C. Thus, 34 g of purified reaction product (98.9 GC %) was obtained (distillation yield: 83.0%). The results of $^1$H-NMR and $^{19}$F-NMR confirmed that this purified reaction product was a mixture of compounds represented by the following formulae:

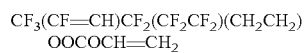

$^1$H-NMR (CDCl$_3$, TMS):
δ5.67-5.81 (CH=CF, CF=CH)
2.45 (CH$_2$CH$_2$)
4.37 (CH$_2$CH$_2$)
6.11 (CH=CH$_2$)
6.40, 5.88 (CH=CH$_2$)
$^{19}$F-NMR (CDCl$_3$, C$_6$F$_6$):
ppm −87.0 to −86.7 (CF$_3$)
−117.6 to −110.4 (CF$_2$CH=CF, CF=CHCF$_2$)
−124.8 (CF$_2$CF$_2$CH$_2$)
−114.5 (CF$_2$CF$_2$CH$_2$)

The invention claimed is:

1. A mixture of fluoroalkyl alcohols represented by the general formulae:

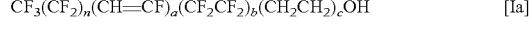 [Ia]

and

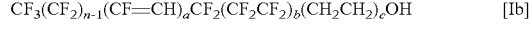 [Ib]

wherein n is an integer of 1 to 5, a is an integer of 1 to 4, b is an integer of 0 to 3, and c is an integer of 1 to 3.

2. A method for producing a mixture of fluoroalkyl alcohols represented by the general formulae:

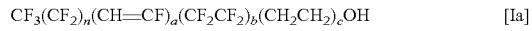 [Ia]

and

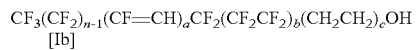
[Ib]

wherein n is an integer of 1 to 5, a is an integer of 1 to 4, b is an integer of 0 to 3, and c is an integer of 1 to 3; which method comprises subjecting to a reaction of a fluoroalkyl iodide represented by the general formulae:

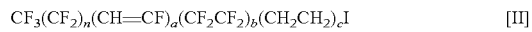 [II]

wherein n, a, b and c are as defined above; with N-methylformamide, followed by hydrolysis in the presence of a basic compound.

* * * * *